United States Patent [19]

Ogawa

[11] Patent Number: 4,891,119
[45] Date of Patent: Jan. 2, 1990

[54] MEDIUM FOR ELECTROPHORESIS HAVING IMPROVED PHYSICAL PROPERTIES

[75] Inventor: Masashi Ogawa, Asaka, Japan

[73] Assignee: Fuji Photo Film Co., Ltd., Kanagawa, Japan

[21] Appl. No.: 651,211

[22] Filed: Sep. 14, 1984

[30] Foreign Application Priority Data

Sep. 14, 1983 [JP] Japan ................................ 58-169579

[51] Int. Cl.$^4$ ................................................. B01K 5/00
[52] U.S. Cl. ............................... 204/299 R; 204/182.8
[58] Field of Search ............. 204/299 R, 180 G, 182.8

[56] References Cited

U.S. PATENT DOCUMENTS 4,415,428 11/1983 Nochumson et al. .......... 204/299 R

Primary Examiner—John F. Niebling
Attorney, Agent, or Firm—Jules E. Goldberg

[57] ABSTRACT

A medium for electrophoresis comprising a polyacrylamide gel formed by crosslinking polymerization of an acrylamide compound and a crosslinking agent in the presence of water, which is characterized in that the medium contains a water-soluble polymer.

7 Claims, No Drawings

MEDIUM FOR ELECTROPHORESIS HAVING IMPROVED PHYSICAL PROPERTIES

BACKGROUND OF OF THE INVENTION

1. Field of the invention

This invention relates to a gel medium for electrophoresis advantageously employable for electrophoresis of biopolymers such as proteins and nucleic acids, and more particularly to an aqueous gel medium for electrophoresis improved in physical properties.

2. Description of prior arts

The electrophoresis can be carried out in the following manner: a membrane medium for electrophoresis prepared by coating or casting a membrane-forming material such as agar, cellulose, cellulose acetate, starch, silica gel or polyacrylamide gel over a support such as glass plate or transparent plastic film is impregnated with a buffer solution or immersed in a buffer solution; on the medium is applied a substance to be analyzed (sample); the applied sample is developed (or resolved) on or in the medium by applying a voltage to both ends of the support and dyed; and then the dyed sample is measured on the optical density to quantitatively determine the components of the sample.

Details of the electrophoresis and medium therefor are given in "Experimental Text for Electrophoresis (5th revision)" editted by Electrophoresis Society of Japan (Bunkodo, 1975), "Modern Electrophoresis" editted by Aoki and Nagai (Hirokawa Shoten, 1973), etc.

Recently, the electrophoresis has been applied to analyze substances originating from a living body; for instance, the electrophoresis has been employed for analyses of proteins originating from a living body to be performed in the course of biochemical analysis for diagnosis, and further employed for analyses of fragments of DNA (deoxyribonucleic acid) to be performed for study of hereditary disease. Thus, the electrophoresis is now widely utilized, and the tests utilizing the electrophoresis are acquiring a greater importance.

As the membrane or sheet for electrophoresis, a filter paper was previously employed, but recently an agarose membrane or a polyacrylamide gel membrane has been employed in view of the properties. Particularly, the polyacrylamide gel membrane showing molecular sieve function is mostly employed at the present time. The polyacrylamide gel membrane can be prepared by crosslinking polymerization of a monomer such as acrylamide and a two-functional crosslinking agent such as N,N'-methylenebisacrylamide under oxygen-free conditions in the presence of water and a polymerization catalyst.

However, the conventional polyacrylamide gel membrane has a serious disadvantage in the membrane properties that the membrane is brittle and easily breakable. For this reason, a polyacrylamide gel membrane is generally prepared by a process involving: introducing an aqueous solution (gel-forming solution or gel solution) containing acrylamide, a crosslinking agent and a polymerization catalyst into a cell formed with spacers having a certain thickness (e.g., 0.3–1 mm) which are provided on a glass plate; covering the introduced gel solution with a glass plate for sealing the gel solution from oxygen; and causing the crosslinking polymerization to prepare the desired gel membrane.

Generally, electrophoresis using a polyacrylamide gel membrane should be provided with slots (caves) for receiving a sample. The conventional gel membrane, however, is very brittle and easily breakable, and accordingly the prepared gel membrane can hardly be subjected to cutting procedure by means of a razor for the purpose of forming the sample slots. For this reason, the sample slots are generally prepared by inserting a sample slot former into a gel-forming solution in advance of performing the gelation reaction. A variety of sample slot formers are known. For instance, a glass plate provided with projections for the formation of sample slots is generally employed in the glass plate-sealing method. The necessity of such additional operation is an obstacle to manufacturing the polyacrylamide gel in a mass scale.

The prepared polyacrylamide gel is horizontally or vertically placed for performing slab electrophoresis. The electrophoresis is performed for a certain period of time under given conditions, and the desired analysis of the components originating from the living body is done after dyeing the electrophoresed gel membrane with Ponceau 3R (Ciba-Geigy), Coomassie Brilliant Blue G-250 (ICI), silver, etc.

SUMMARY OF THE INVENTION

An object of the present invention is to provide a medium for electrophoresis which is improved in the unfavorable feature of the conventional polyacrylamide gel membrane, in which the unfavorable feature stems mainly from the composition of the gel medium. More specifically, the invention is to provide a gel membrane which is not easily broken, easily handled and moreover readily processed for forming sample slots in optional shapes.

Another object of the invention is to provide a polyacrylamide gel medium which is satisfactory in electrophoretic characteristics such as resolution and migration velocity, and is remarkably excellent in total characteristics including the function as molecular sieve, as compared with the conventional medium.

There is provided by the present invention a medium for electrophoresis comprising a polyacrylamide gel formed by crosslinking polymerization of an acrylamide compound (hereinafter, simply referred to as "monomer") and a crosslinking agent in the presence of water, which is characterized in that the medium contains a watersoluble polymer.

In the present invention, the aqueous gel medium can be prepared by dissolving or dispersing an acrylamide compound and a crosslinking agent in an aqueous medium and performing the crosslinking polymerization therebetween in the aqueous medium to form an aqueous gel medium. Hereinafter, the term "dissolving (in water)" means to include both "dissolving (in water)" and "dispersing (in water)", and the term "aqueous solution" means to include both "aqueous solution" and "aqueous dispersion", unless otherwise indicated. The term of "aqueous medium" is used to include an aqueous mixture of water and an organic solvent, the latter being optionally added.

DETAILED DESCRIPTION OF THE INVENTION

Examples of the acrylamide compound employable in the invention include acrylamide and its homologues such as N-methylacrylamide, N,N-dimethylacrylamide, N-(hydroxymethyl)acrylamide and diacetonacrylamide, and these compounds may be employed independently or in combination. Acrylamide is most preferable among these acrylamide compounds, and said acrylamide can be also preferably employed in combination with one or more of other acrylamide compounds.

As the crosslinking agent employable to obtain the polyacrylamide gel of the invention, a known crosslinking agent described, for instance, in "Electrophoresis" 1981, 2, 213–228 can be employed singly or in combination. Examples of the crosslinking agent include bifunctional compounds such as N,N'-methylenebisacrylamide (BIS), N,N'-propylenebisacrylamide (PBA), diacrylamide dimethylether (N,N'-oxydimethyleneacrylamide), 1,2-diacrylamide ethyleneglycol (DEG), 1,3-diacryloylethyleneurea, ethylene diacrylate (EDA), N,N'-diallyltartardiamide (DATD), and N,N'-bisacrylylcystamine (BAC). The crosslinking agent can be employed in an amount of approx. 1 to 30 wt. %, preferably approx. 3 to 10 wt. %, based on the total weight of the monomer (i.e., acrylamide compound) and the crosslinking agent. The gel concentration preferably is in a range of approx. 3 to 30 wt/v % (total weight of monomer and crosslinking agent per total volume of gel medium comprising monomer, crosslinking agent and aqueous medium), the concentration being in accordance with the indicated by S. Hjerten in "Arch. Biochem. Biophys." 1 (Suppl.), 147 (1962).

The medium for electrophoresis of the invention may contain an anionic surfactant as a modifier. The use of the anionic surfactant is advantageous particularly in the electrophoretic analyses of proteins or conjugated proteins (e.g., lipoproteins, glycoproteins, etc.)

Examples of the anionic surfactant include alkylsulfates, particularly alkylsulfates having a long chain alkyl group of at least 10 carbon atoms. The cation contained therein for formation of the salt generally is an alkali metal ion such as sodium ion, potassium ion, or lithium ion. Sodium ion is preferred from an economical viewpoint. The aklylsulfates preferably are dodecylsulfates (salts of sodium, potassium, lithium, etc.), and particularly preferred is sodium dodecylsulfate (SDS). The introduction of the anionic surfactant into the gel medium is advantageous for separation of proteins and conjugated proteins, as well as for determination of molecular weight thereof. The anionic surfactant (modifier) is contained in the gel-forming solution in an amount of approx. 0.05 to 2.0 wt/v % (weight per volume of the gel-forming solution), preferably approx. 0.1 to 1.5 wt/v %.

The gel medium of the invention may contain an oxidation inhibitor. The oxidation inhibitor can be chosen from various compounds heretofore known as oxidation inhibitors employable for the gel medium for electrophoresis. Examples of the oxidation inhibitor include 1,4-dithiothreitol and 2-mercaptoethanol.

As the water-soluble polymer, a water-soluble polymer of the addition polymerization type or condensation polymerization (i.e., polycondensation) type can be used. Examples of the polymer of the addition polymerization type include non-ionic water-soluble polymers such as polyvinyl alcohol, polyvinyl pyrrolidone, and polyacrylamide. Examples of the polymer of the condensation polymerization type include non-ionic water-soluble polyalkylene glycols such as polyethylene glycol and polypropylene glycol. The water-soluble polymer of a molecular weight in the range of from approx. 10,000 to 1,000,000 is preferably used. Among these water-soluble polymers, polyacrylamide and polyethylene glycol are preferable. The water-soluble polymer is used in a range of approx. 1 to 100 wt. %, preferably, approx. 5 to 50 wt. %, based on the total weight of the monomer and crosslinking agent.

According to the present invention, the addition of a water-soluble polymer serves to impart elasticity to the gel medium, and thus modified gel medium is still elastic even if it is dried. Thus, the gel medium is so improved as to be free from the brittleness, whereby the gel medium becomes hardly breakable. Further, the viscosity of the gel medium can be controlled by selecting the molecular weight and amount of the water-soluble polymer to be incorporated.

A pH buffer agent can be contained in the gel medium of the invention. Any buffer agent which is able to buffer a solution to a range of pH 2.5 to 10.0 can be used. Buffer agents employable in the invention are described in publications such as "Chemistry Handbook, Fundamental Edition" compiled by The Chemical Society of Japan (Maruzen Ltd., Tokyo, 1966) pages 1312–1320; "Modern Electrophoresis" editted by Aoki and Nagai (Hirokawa Shoten, 1973), pages 320–322; "Data for Biochemical Research" compiled by R.M.C. Dawson et al., second edition (Oxford at the Clarendon Press, 1969) pages 476–508; "Biochemistry" 5, 467 (1966); and "Analytical Biochemistry" 104, pages 300–310 (1966).

Examples of the buffer agent include a buffer agent containing barbital, a buffer agent containing tris(hydroxymethyl)aminomethane (Tris), a buffer agent containing phosphate, a buffer agent containing borate, a buffer agent containing acetic acid or acetate, a buffer agent containing citric acid or citrate, a buffer agent containing lactic acid or lactate, and a buffer agent containing glycine; as well as N,N-bis(2-hydroxyethyl)glycine (Bicine), N-2-hydroxyethylpiperazine-N'-2-hydroxypropane-3-sulfonic acid (HEPPSO) or its salt, N-2-hydroxyethylpiperazine-N'-3-propanesulfonic acid (EPPS) or its salt, N-tris(hydroxymethyl)methyl-3-aminopropanesulfonic acid (TAPS) or its salt. Preferable examples of the buffer agent include potassium dihydrogenphosphate-disodium hydrogenphosphate, Tris-sodium borate, Tris-sodium borate-EDTA.2Na, Tris-citric acid, sodium barbital-sodium acetate, sodium barbital-hydrochloric acid, barbital-sodium barbital, acetic acid-sodium acetate, lactic acid-sodium lactate, citric acid-disodium hydrogenphosphate, Bicine, HEPPSO, sodium salt of HEPPSO, EPPS, sodium salt of EPPS, TAPS, sodium salt of TAPS, etc.

The gel medium used in the invention is formed by radical crosslinking-polymerization between the monomer such as acrylamide and the bifunctional compound (crosslinking agent) in an aqueous medium in which the water-soluble polymer is dissolved almost homogeneously. The gel is assumed to have a structure in which the watersoluble polymer is dispersed in the three dimensional crosslinked polymer formed by the reaction of the monomer and cross-linking agent, and the water-soluble polymer is dispersed and is further entangled with the three dimensional crosslinked polymer structure. This structure is one of the characteristic features of the gel medium of the invention.

The crosslinking polymerization can be initiated by a known method, for instance, in the presence of a peroxide and/or under irradiation of utltraviolet rays. The reaction can be further accelerated by heat and irradiation with ultraviolet rays.

As the polymerization catalyst, a known low temperature-polymerization initiator such as those described in "Electrophoresis" 1981, 2, 213–219, ibid. 1981, 2, 220–228; and "Modern Electrophoresis" editted by Aoki and Nagai (Hirokawa Shoten, 1973) can be used. Examples of the initiator include a mixture of β-dimethylaminopropionitrile (DMAPN) and ammonium peroxodisulfate, a mixture of N,N,N',N'-tetramethylethylenediamine (TEMED) and ammonium peroxodisulfate, a mixture of TEMED and riboflavin, a combination of a mixture of TEMED, riboflavin and hydrogen peroxide, and irradiation with ultra-violet rays. The radical reaction initiator can be employed in an amount of approx. 0.3 to 5 wt. %, preferably approx. 0.5 to 3 wt. %, based on total amount of the monomer and cross-linking agent.

In the case that the gel medium of the invention is used in the form of layer or membrane, a gel layer or gel membrane can be prepared by a process in which a gel forming solution is coated by a known method on an electric insulation support having a smooth hydrophilic surface, and the gel forming solution is crosslinked to polymerization thereon. Examples of the support include glass plate, hydrophilic polymers in the form of plate or sheet, and other polymers (e.g., polyethylene terephthalate, polycarbonate of bisphenol A, polyvinyl chloride, vinylidene chloride - vinyl chloride copolymer, polymethylmethacrylate, polyethylene, polypropylene, cellulose acetate, and cellulose acetate propionate) in the form of plate or sheet, a surface of which is made hydrophilic by a known surface treatment. Examples of the treatment employable to make the surface of these polymers hydrophilic include known methods such as irradiation with ultraviolet rays, glow discharge treatment, corona discharge treatment, flame treatment, electron beam treatment, chemical etching, or electrochemical etching.

In the case that the gel forming solution is crosslinked to polymerization on the surface of the support, the surface of the gel forming soultion can be covered with a cover film, sheet, or plate. The same material as employable for the support can be employed as the cover film, sheet, and plate.

A polyol compound such as glycerol or ethylene glycol can be contained in the gel medium of the invention as a wetting agent. The polyol compound can be introduced in an amount of approx. 1 to 40 wt. % based on the volume of the aqueous gel medium. Glycerol is particularly preferable among the polyol compounds. The addition of the wetting agent serves to keep the gel medium from excessive dryness possibly caused by evaporation of water during storage of the medium, whereby preventing the medium from turning brittle or cracking caused by the excessive dryness. Thus, the improvement of physical properties of the gel medium is accomplished.

The gel medium of the invention can be employed for the horizontal or vertical plate-type electrophoresis, disc electrophoresis, etc. by known methods described, for instance, in the aforementioned texts.

The present invention will be more clearly understood with reference to the following examples.

EXAMPLE 1

A glass plate cell with thickness of 0.5 mm was constructed using two glass plates with smooth surface and spacer with thickness of 0.5 mm. The acrylamide gel composition solution (gel-forming solution) set forth in Table 1 was poured into the cell and crosslinked to polymerization to form a polyacrylamide gel membrane. One glass plate was removed after gelation was complete, and sample slots were provided by cutting the polyacrylamide gel membrane by means of a sharp cutter.

TABLE 1

| Gel Composition | | | | |
|---|---|---|---|---|
| | \multicolumn{4}{c}{Sample Number} |
| | 1 | 2 | 3 | 4 |
| Gel Composition | | | | |
| Acrylamide | 9.5 g | 9.5 g | 9.5 g | 9.5 g |
| Bis | 0.5 g | 0.5 g | 0.5 g | 0.5 g |
| Polyacrylamide (mean M.W. 50,000) | None | 1.25 g | 2.5 g | None |
| Polyacrylamide (mean M.W. 800,000) | None | None | None | 1.25 g |
| Disodium hydrogenphosphate. 12 hydrates | 3.58 g | 3.58 g | 3.58 g | 3.58 g |
| Sodium dihydrogenphosphate. 12 hydrates | 0.33 g | 0.33 g | 0.33 g | 0.33 g |
| SDS | 0.10 g | 0.10 g | 0.10 g | 0.10 g |
| Water | \multicolumn{4}{c}{(added to make 100 ml)} |
| Polymerization Initiator | | | | |
| Ammonium peroxodisulfate (5 wt. % aqueous sol.) | 1.3 ml | 1.3 ml | 1.3 ml | 1.3 ml |
| TEMED | 33 μl | 33 μl | 33 μl | 33 μl |

As for Sample No. 1 (reference gel membrane), the cut end cracked and the membrane was broken, and accordingly sample slots of sharp edge could not be formed. On the other hand, as for Samples No. 2 to No. 4 (gel membrane according to the invention), sample slots showing sharp edge was easily formed.

The gel membrane obtained as above was again covered with a glass plate, and the electrophoresis was performed by the conventional method to observe electrophoresed dye pattern.

As for Sample No. 1, serious disorder of the electrophoresed dyes was observed. As for Samples No. 2 to No. 4, no disorder was observed, and uniform electrophoresed patterns were observed.

Accordingly, it is apparent that the problem in brittleness of the gel membrane is remarkably improved by the present invention, as compared with the conventional gel membrane.

EXAMPLE 2

Gel membranes were prepared using the same gel compositions as described in Example 1. For reference, a membrane was prepared from the same composition as that of Sample No. 1, except that a sample slot former was employed for the preparation of the sample slots (Sample No. 1-A: reference gel membrane).

As for Samples No. 2 to No. 4 (gel membrane according to the invention), sample slots showing sharp edge were again formed easily. As for Sample No. 1 (reference gel membrane), the cut end again cracked and the membrane was broken, and accordingly sample slots of sharp edge were not formed.

Electrophoresis using standard proteins was performed on these gel membrane. As the standard proteins, cytochrome c (M.W. 12,400), chymotrypsinogen A (M.W. 25,000), ovalbumin (M.W. 45,000), and bovine serum albumin (M.W. 67,000) were employed.

Sample No. 1-A and Samples No. 2 to No. 4 exhibited normal electrophoresed patterns, but Sample No. 1 exhibited a disordered electrophoresed pattern. The dyeing was done by immersing the gel medium in an aqueous solution of Coomassie Blue R-250 (0.1 %).

Accordingly, it has been confirmed that a gel membrane according to the present invention exhibits satisfactory electrophoresis characteristics, being improved in the brittleness.

EXAMPLE 3

Polyacrylamide gel membranes were prepared in the same manner as in Example 1 except that the solid polyacrylamide (water-soluble polymer) was replaced with polyethylene glycol (average molecular weight 200,000). Thus prepared membranes were subjected to the same electrophoresis. It was observed that the gel membranes according to the present invention exhibited satisfactory electrophoresis characteristics, as well as that the brittleness of membranes was remarkably improved and the gel membranes were freely cut for the formation of sample slots.

Accordingly, the advantage of the invention has been again confirmed.

I claim:

1. In a medium for electrophoresis comprising a polyacrylamide gel formed by crosslinking polymerization of an acrylamide compound and a crosslinking agent in the presence of water, the improvement which comprises said polyacrylamide gel containing a water-soluble polymer of a molecular weight in the range of 10,000 to 1,000,000 selected from the group consisting of a polymer of an addition polymerization type and a polymer of a polycondensation type, said water-soluble polymer being incorporated into the gel in the form of a polymer in an amount of 1 to 100 wt. % based on the total weight of the acrylamide compound and crosslinking agent.

2. The medium for electrophoresis as claimed in claim 1, in which an anionic surfactant is contained.

3. The medium for electrophoresis as claimed in claim 2, in which said anionic surfactant is an alkylsulfate.

4. The medium for electrophoresis as claimed in claim 3, in which said alkylsulfate is sodium dodecylsulfate.

5. The medium for electrophoresis as claimed in claim 1 in which said crosslinking agent is contained in a range of from 1 to 30 wt. %, based on the total weight of the acrylamide compound and crosslinking agent.

6. The medium for electrophoresis as claimed in any of claims 3 or 4, in which said anionic surfactant is contained in a range of from 0.05 to 2.0 wt/v % based on the volume of the polyacrylamide gel.

7. The medium for electrophoresis as claimed in claim 1, in which said water-soluble polymer is polyacrylamide or polyalkylene glycol.

* * * * *